United States Patent
Blomsma et al.

(10) Patent No.: US 7,079,621 B2
(45) Date of Patent: Jul. 18, 2006

(54) VERTICAL TRANSMISSION DIFFRACTION ANALYSIS

(75) Inventors: Erwin Blomsma, Haarlem (NL); Adriaan Jan van Langevelde, Almere (NL)

(73) Assignee: Avantium International B.V., Amsterdam (NL)

( * ) Notice: Subject to any disclaimer, the term of this patent is extended or adjusted under 35 U.S.C. 154(b) by 0 days.

(21) Appl. No.: 10/491,078

(22) PCT Filed: Oct. 3, 2002

(86) PCT No.: PCT/EP02/11193

§ 371 (c)(1),
(2), (4) Date: Mar. 29, 2004

(87) PCT Pub. No.: WO03/031959

PCT Pub. Date: Apr. 17, 2003

(65) Prior Publication Data

US 2005/0069084 A1  Mar. 31, 2005

(30) Foreign Application Priority Data

Oct. 3, 2001 (EP) .................................. 01203756

(51) Int. Cl.
*G01N 23/207* (2006.01)

(52) U.S. Cl. .......................................... 378/73; 378/79
(58) Field of Classification Search ............ 378/70–81
See application file for complete search history.

(56) References Cited

U.S. PATENT DOCUMENTS

| | | | | |
|---|---|---|---|---|
| 3,354,308 A | * | 11/1967 | Engel et al. ................... | 378/47 |
| 3,378,684 A | * | 4/1968 | Mentink et al. ............. | 250/428 |
| 4,821,303 A | * | 4/1989 | Fawcett et al. ............... | 378/80 |
| 5,629,524 A | | 5/1997 | Stettner et al. ........ | 250/370.09 |
| 6,122,344 A | | 9/2000 | Beevor ......................... | 378/88 |
| 6,371,640 B1 | * | 4/2002 | Hajduk et al. .............. | 378/208 |
| 6,507,636 B1 | | 1/2003 | Lehmann ...................... | 378/79 |
| 6,859,520 B1 | * | 2/2005 | He et al. ....................... | 378/79 |
| 2004/0223586 A1 | * | 11/2004 | He et al. ....................... | 378/86 |

FOREIGN PATENT DOCUMENTS

| WO | WO 00/36405 | 6/2000 |
|---|---|---|
| WO | WO 02/057763 | 7/2002 |

OTHER PUBLICATIONS

Chayen, et al. An Automated System for MicroBatch Protein Crystallization and Screening 10565 Journal of Applied Crystallography 23(1990) Copenhagen, DK.
JP 2000212137 (Abstract) Feb. 8, 2000.

* cited by examiner

*Primary Examiner*—Edward J. Glick
*Assistant Examiner*—Jurie Yun
(74) *Attorney, Agent, or Firm*—Hoffmann & Baron, LLP

(57) ABSTRACT

The present invention relates to a method for performing a transmission diffraction analysis of an analyte on a support surface, wherein the method comprises: irradiating said analyte with a radiation beam generated by a source of radiation, and detecting said radiation after passing through the analyte. The method is characterised in that irradiation is performed such that the radiation beam strikes the analyte in a substantially vertical and substantially perpendicular direction. Further the present invention relates to an apparatus for performing a transmission diffraction analysis.

25 Claims, 3 Drawing Sheets

VERTICAL TRANSMISSION DIFFRACTION ANALYSIS

CROSS-REFERENCE TO RELATED APPLICATIONS

This application is the National Stage of International Application No. PCT/EP02/11193, filed Oct. 3, 2002, which claims the benefit of European Application No. EP 01203756.0, filed Oct. 3, 2001, and of U.S. Provisional Application No. 60/326,453, filed Oct. 3, 2001, the contents of all of which are incorporated by reference herein.

FIELD OF THE INVENTION

The present invention relates to a method for performing a transmission diffraction analysis of one or more analytes on a support surface, wherein the method comprises:
 irradiating said analyte with a radiation beam generated by a source of radiation, and
 detecting said radiation after passing through the analyte.

BACKGROUND OF THE INVENTION

WO-A-00/36405 discloses an apparatus and method for characterising libraries of different materials using X-ray scattering. The apparatus includes an X-ray beam directed at the library, which library contains an array of elements each containing a different material, a chamber which houses the library and a beam line for directing the X-ray beam onto the library in the chamber. During the characterisation, the X-ray beam scatters off of the element and a detector detects the scattered X-ray beam in order to generate characterisation data for the element.

U.S. Pat. No. 6,111,930 discloses an X-ray diffractometer suitable for detection in reflection mode as well as transmission mode. In the reflection mode the support for an analyte is in horizontal position. In order to perform an analysis in transmission mode the support is rotated about a horizontal axis of the goniometer, so that the support is in an essentially vertical position.

Scattering of incident radiation such as X-rays, gamma rays, cathode rays, etc. from a sample of material can yield information about the atomic structure of the material. When such a beam of radiation strikes a sample, a pattern of diffracted radiation is created, which has a spatial intensity distribution that depends on the wavelength of the incident radiation and the atomic structure of the material and that can be recorded on a suitable detector. Diffraction analysis is the method of choice for studying crystalline materials, crystallisation behaviour and liquid, gel or solid phase, or phase transitions of materials.

Crystallisation is in general considered as the separation or precipitation out of a liquid environment or the settling into the solid phase of a melt. The basic approach to crystallisation of substance from a solution is usually fairly simple. The molecule(s) to be crystallised is (are) dissolved or suspended and subsequently subjected to conditions that affect the solubility of the molecule or molecular complex in solution. This can be achieved by removal of the solvent or by the addition of other compounds that reduce the solubility, optionally in combination with variation of other factors such as temperature, pressure or gravitational forces. When the conditions are right, small nuclei will form from which crystals will grow. However, the relations between the crystallisation conditions and the crystal packing or even the occurrence of crystallisation is generally not well understood. The optimisation of the crystallisation conditions and the identification of conditions that lead to one specific type of molecular packing in the crystal are largely based on trial and error. The determination of the optimal crystallisation conditions can therefore be a laborious and time-consuming process.

When many different samples have to be submitted to diffraction analysis, the efficiency of the analysis is of the utmost importance. By far the most efficient way of analysis in terms of amount of sample required, measuring time and signal-to-noise ratio is the transmission geometry of diffraction. In the transmission diffraction mode, the entire fan of forwardly diffracted radiation is measured by a position sensitive radiation detector, unlike in the reflection mode, where only a small section of the fan of diffracted radiation is measured. However the transmission geometry of powder diffraction is hardly ever used, since it can be compromised by strong absorption in the case of very electron dense samples. Also, very thin analyte films have to be used to obtain a suitable resolution. Nevertheless, many organic samples, like drugs or drug candidates, are sufficiently transparent not to compromise the quality of the powder diffraction data. In these and many other cases, applying the transmission geometry to such samples will substantially reduce the measuring time required to obtain a signal-to-noise ratio that is sufficient for further characterisation. To increase throughput, an automated array, allowing for fast measuring of many analytes without human interference, is highly desirable. To this end, a convenient way of mounting all samples simultaneously in an array format, and automatically translating said array during the analysis from one sample to the next can be employed.

In all set-ups for diffraction in the transmission geometry that have been used up till now, as is also the case in WO-A-00/36405, the radiation beam is horizontal and the analyte support mounted substantially vertical, implying that any sample either needs to be bonded by some physical means to a (semi-)translucent substrate, or enclosed in a container, e.g. a thin-walled glass or quartz capillary. In this "horizontal" set-up the analytes that are formed during a certain experiment have to be removed to another container for transmission diffraction analysis. This can be inconvenient, because it is time-consuming, and it involves an extra processing step. Removal of an analyte further involves risks of the crystallised structure of the analyte being disrupted, or the analyte being contaminated. Furthermore, it is not convenient to study phase transitions of the analyte using the known apparatus, when one of the phases is liquid as the analyte may drop off or shift relative to the radiation beam.

Furthermore, until presently, for successful crystallisation to take place, a large amount of analyte is required.

The above problems are particularly pertinent in the case of e.g. the early development of new substances or in high throughput experimentation wherein often only a very small amount of analyte is available. High throughput experimentation is known in the art and is used for simultaneously conducting a large number of experiments using a plurality of vessels, optionally with different reaction conditions. High throughput experimentation is used for instance in the pharmaceutical industry for discovery and development of new and useful drugs and in the field of catalysts for the development of new catalysts.

OBJECT OF THE INVENTION

It is an object of the present invention to provide a new and alternative way of performing a transmission diffraction analysis of an analyte, having a high signal-to-noise ratio, especially when the amount of analyte available is very small.

SUMMARY OF THE INVENTION

The above and other objects can be achieved by a method for performing a transmission diffraction analysis of an analyte, wherein the method comprises:

irradiating said analyte with a radiation beam generated by a source of radiation, and detecting said radiation after passing through the analyte, characterised in that irradiation is performed such that the radiation beam strikes the analyte in a substantially vertical and substantially perpendicular direction in relation to the support surface.

Using the method according to the present invention a surprisingly simple, very quick and efficient way of simultaneously analysing a plurality of analytes has become possible. Also, the method according to the present invention provides for a surprisingly elegant and convenient way to study phase transitions of analytes, when one of the phases is liquid. Further the method allows easy automation.

According to the present invention, with "substantially vertical and substantial perpendicular direction" is meant any direction which meets a horizontal plane (i.e. a plane substantially parallel to the earth's surface) at such an angle that no additional attachment of the analytes to a support on which (or a container in which) the analyte is placed is required. Preferably this angle is about 90 degrees. However, the person skilled in the art will readily understand that also other angles between the horizontal plane and the direction of the beam of radiation used in the method according to the invention may be used. Suitably, this angle is at least 75 degrees.

The person skilled in the art will understand that the source of radiation may provide itself a substantial vertical direction of the beam of radiation. Alternatively, the direction of the beam of radiation, provided by a source of radiation of the invention, may be changed before performance of a transmission diffraction analysis, for instance by using at least one mirror.

According to the present invention, with "radiation" any radiation is meant which can be used for performing a transmission diffraction analysis of an analyte, such as X-rays, gamma rays, cathode rays. In use, the source of radiation may be located above the analyte, pointing downwards; alternatively said source of radiation may be located underneath the analyte, pointing upwards.

An "analyte" is defined herein as a sample or a compound of which the diffraction or crystallisation behaviour is to be determined. Such an analyte may be a chemical substance, or a mixture of different substances. Also, at least one crystal form of the substance may be known or expected to exist. An analyte of the invention may comprise an organic or organometallic molecular compound, such as a pharmaceutically active molecule or catalyst-ligand complex or a dimer, salt, ester, solvate or functional part thereof. An analyte of the present invention may also comprise a biomolecule, for instance a nucleic acid (such as DNA, RNA and PNA), a polypeptide, peptides, glycoprotein and other proteinaceous substances, a lipoprotein, protein-nucleic acid complex, carbohydrate, biomimetic or a functional part, derivative and/or analogue thereof.

The present invention allows for the simultaneous screening of a plurality of analytes, e.g. placed in arrays, without having to physically remove the analytes from the container in which said analytes are prepared, as long as said containers are translucent to the radiation which is used. Thus, preferably, said analyte is not removed to another container or support. The alignment such that the direction of the radiation beam is substantially vertical, is a prerequisite for achieving a transmission geometry for diffraction of an analyte in an open container or resting on a support, without having to physically or otherwise attach said analyte to said container or support. It is now possible with the method of the invention to analyse said analyte in a 2-dimensional array, for instance a microtiter plate.

Therefore, according to a preferred embodiment of the method according to the present invention, the analyte is placed on a support, without any additional attachment. This means that the analyte may be bonded to a support by no other means than the force of gravity.

Herewith contamination of the analyte can be prevented, or at least minimised.

The present invention is especially useful in powder diffraction analysis, especially when a plurality of small amounts of analytes in arrays are to be analysed simultaneously. The method of the invention is ideally suited for detecting both wide and small angle scattering from said analytes, when formed in situ in a translucent container. In this particular embodiment, the samples are crystallised in said container and analysed without having to harvest the samples onto a suitable carrier. The plurality of containers can subsequently be presented for diffraction analysis, which also increases the potential for further automation of sample analysis in general.

The analyte may be provided in a specially designed substrate similar to a microtiter plate, fabricated from material that is translucent to X-rays. Said substrate is preferably chemically inert to the substances and solvents employed and is preferably transparent to the detection technique used, e.g. X-ray transparent in case of X-ray diffraction technique. The substrate is preferably also transparent to visual light (ca 200 nm to 1000 nm) to allow visual or optical inspection. The substrate is preferably also capable of transferring heat, thereby allowing for temperature variations. Examples of arrays are 8 by 12 mm up to 32 by 48 mm, with orthogonal centre to centre distance varying from 2 to 10 mm between the containers or wells of the substrate. Of course, the substrate may be provided with means for controlling and/or adjusting the atmosphere conditions in or directly above the cells. For this purpose the support medium is for instance fitted with sealing devices or sealing substances which seal off individual cells or groups of cells. Balls, plates, caps, inert liquids like paraffin oil, silicon oil, etc. can be provided for said sealing purposes. In this respect it is noted that the sealing devices and/or sealing substances do not necessarily (and preferably do not) attach the analyte to the support, but are provided for controlling the atmosphere in or directly above an individual cell or a group of cells.

With the method of the invention, determination of diffraction characteristics of a crystallised analyte can conveniently be carried out in a provided array in which the crystallisation method has been carried out (in situ). In transmission diffraction geometry this requires that the array itself is transparent to diffraction or that the background diffraction pattern from the array is determined and the obtained diffraction data from the crystal in the array are corrected for this background pattern. The advantage of using a transmission geometry over more conventional reflection geometry of this diffraction experiments, is that substantially more signal is measured per mass unit of analyte. It is thus possible to use milligram, preferably microgram, nanogram or picogram amounts of material and still achieve an improved throughput.

Although the art generally teaches that large quantities of material are required for successful crystallisation it has been shown that sub-microgram quantities can be used for small molecules (molecular weight in the order of less than 500 grams per mole) and even down to 1 nanogram quantities for proteins (molecular weight in the order of more than 5000 grams per mole). Because of the small volumes that can be used in the methods according to the invention, availability of analytes is less of a problem and rapid testing of numerous conditions and easy adjustment of relevant conditions is easily obtained. A method of the invention is thus advantageously used when only minute quantities of the analyte are available, for instance in an early stage of the research. Thus, one embodiment of the invention provides a method according to the invention, wherein the amount of said analyte is less than 1 microgram.

Major advantages of the method according to the invention are that automated set-up of the experiments is generally quicker for small volumes, the automated detection of crystals in an array of conditions is quicker as more samples can be tested simultaneously, less material is required thereby reducing wastage, more tests can be performed given the amount of material available, the chance that the conditions under which crystallisation is achieved are identified significantly increases and the chances of identification of different polymorphic forms increases likewise.

In a further aspect the present invention provides an apparatus for performing a transmission diffraction analysis of an analyte, wherein the apparatus comprises:

a source of radiation being adapted to direct a radiation beam to the analyte;

a support for supporting the analyte, which support is translucent to the radiation; and a detector for detection of the radiation passed through the analyte, wherein the source of radiation, the support for the analyte and the detector are positioned such that the radiation beam generated by the source of radiation can strike the analyte in a substantially vertical and substantially perpendicular direction. As support e.g. an open container or a small plate of translucent material may be used.

As has been described above, a source of radiation may provide an essentially vertical beam of radiation which can be used directly. However, alternatively, the direction of a beam of radiation of an apparatus of the invention may artificially be made substantially vertical for performance of a transmission diffraction analysis, for instance by use of at least one mirror.

The apparatus according to the present invention is very suitable for high throughput experimentation, and to this end the support of the apparatus is designed for supporting a plurality of analytes. The support may be in the form of an array of translucent containers as mentioned above.

Further the present invention relates to the use of the method or the apparatus according to the invention for detection and recording powder diffraction patterns of the analyte. Herewith a powder diffraction pattern can easily be obtained.

Further the present invention relates to the use of the method or the apparatus according to the invention for screening phase behaviour of the analyte, more in particular crystallisation behaviour in liquid, gel or solid phase of an analyte. Said analyte may be an organic molecule, for instance a pharmaceutically interesting compound or complex, oligomer, salt, ester or solvate thereof, or an organo-metallic molecule such as a catalyst for homogeneous catalysis, etc. Preferably the method for screening the phase behaviour of an analyte is carried out in an array of separate cells, whereby each cell contains a different composition. When a change in phase behaviour occurs, this is detected and can be correlated to the specific composition and conditions under which the screening is taking place. Using the method or apparatus according to the invention, the analyte will not drop off from the substrate when a change in phase behaviour occurs, or shift relative to the beam.

According to another aspect of the present invention it relates to the use of the method or apparatus of the invention for detecting polymorphism of the analyte. Herewith the present invention provides an easy way of determination of crystallisation conditions that allow for the growth of different crystal forms of the analyte, thus enabling the identification of polymorphic forms of the analyte. This is valuable information, for instance in the case of a pharmaceutical compound of interest whereby polymorphs of said pharmaceutical compound can each have different physical properties or different properties in terms of biological activity. Official approval such as from the United States' Food and Drug Administration of a specific and well defined drug cannot be transferred to another polymorph of the sample, although the chemical nature of the constituting molecules is identical. It is therefore very important that the various polymorphs are discovered and identified in order to gain an understanding of their biological properties.

Hereinafter the present invention will be illustrated in more detail by a drawing.

DETAILED DESCRIPTION OF PREFERRED EMBODIMENTS

Figure 1:
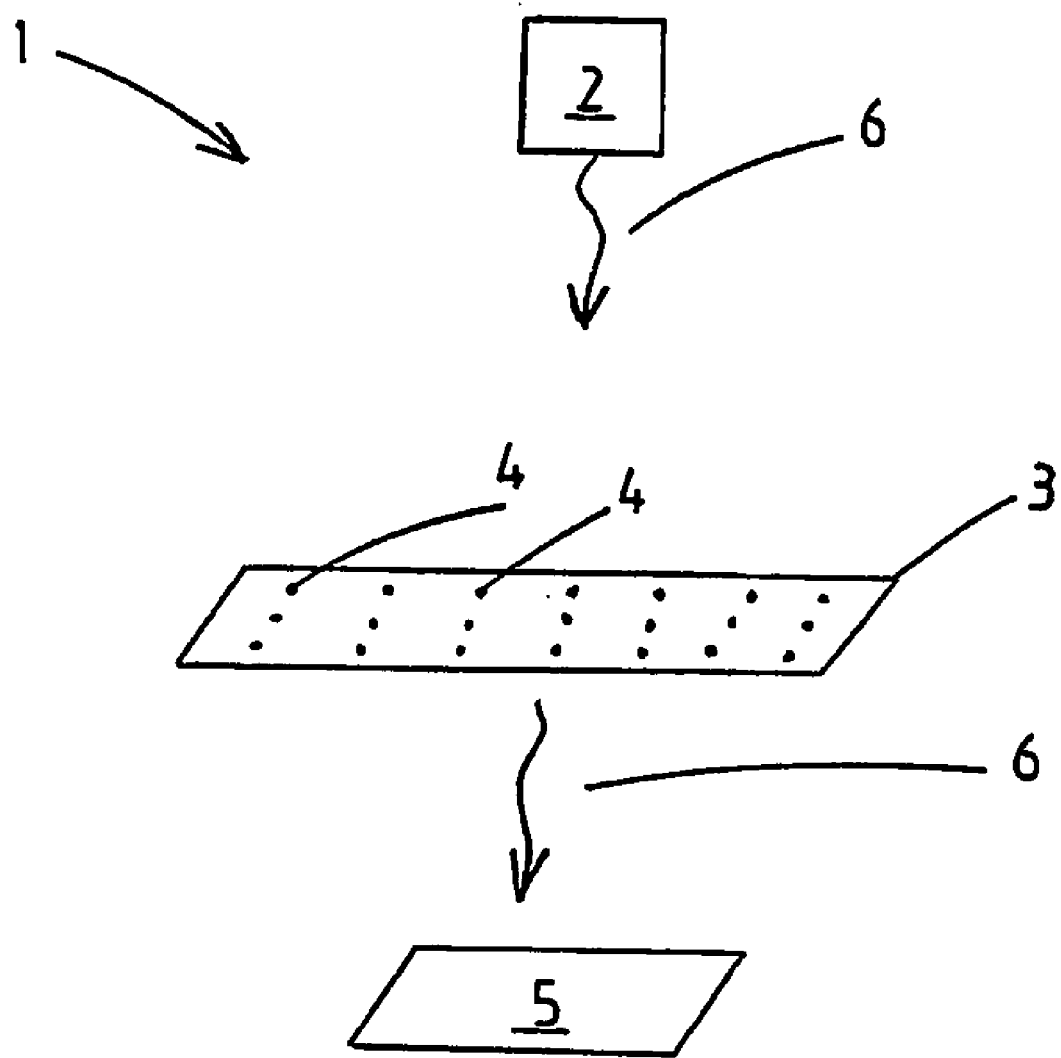
FIG. 1 is a diagram of a transmission mode X-ray diffraction analysing apparatus in accordance with the present invention.

FIG. 1 shows a diagram of an exemplary transmission mode X-ray diffraction analysing apparatus 1 in accordance with the present invention. The apparatus 1 comprises a source 2 of intense X-ray radiation 6 such as a conventional X-ray tube, an array 3 such as a translucent microtiter plate for supporting a plurality of analytes 4, and a detector 5 for detection of the radiation passed through the analyte 4. In the shown embodiment the source 2 of X-ray radiation 6 is located above the analyte 4. The detector 5 for the radiation is in the shown embodiment located on the opposite end of the analyte 4 from the source of radiation 2, such that the radiation 6 is detected and recorded after passing through the analyte 4. The detector 5 may be any suitable detector, such as a stimulable phosphor image plate detector. Preferably the detector 5 is a position sensitive 2D radiation detector.

In use a beam of X-rays 6 is generated by the radiation source 2, and directed to one of the analytes 4 positioned in the array 3. The beam of X-rays 6 strikes the analyte 4 positioned on the array 3 in a substantially vertical and substantially perpendicular direction, and the diffracted radiation scatters from the analyte 4 in a pattern which is recorded in the detector 5. Subsequently, a further analyte 4 is analysed.

The person skilled in the art will understand that many modifications may be made. For instance, the detector 5 may be located above the array 3 of analytes 4, while the X-ray source 2 is placed beneath the analytes 4.

Figure 2:
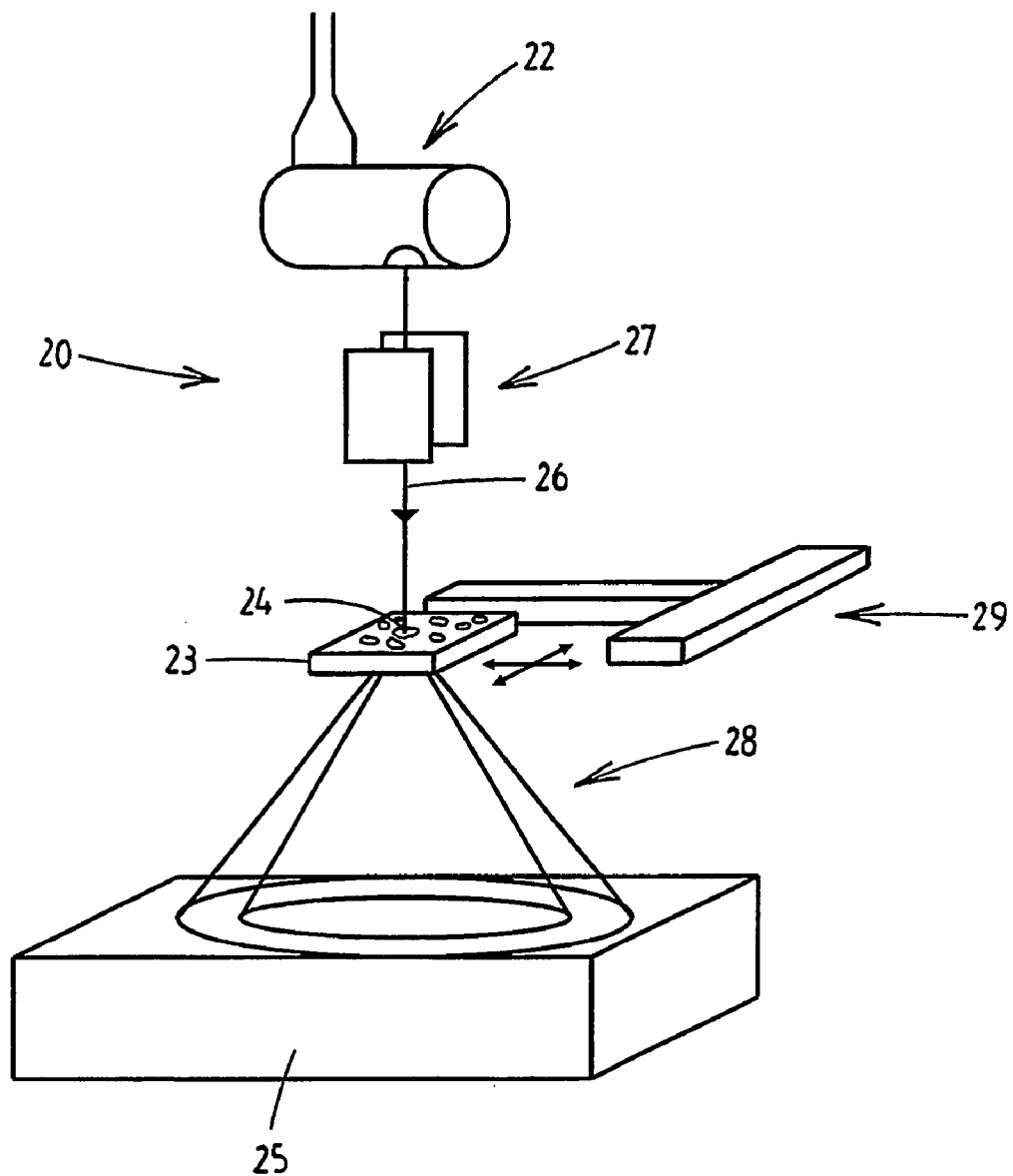
FIG. 2 shows schematically a preferred embodiment of a transmission diffraction analysis apparatus according to the invention.

FIG. 2 schematically shows a transmission diffraction analysis apparatus 20 comprising a source 22 of radiation generating a radiation beam 26, which is oriented vertically and downwards onto a common support 23 for multiple analytes 24. The support 23 is held in horizontal orientation and the analytes 24 are placed in a two-dimensional array on said support 23.

The beam 26 is directed onto one of said analytes 24 and passes through focussing means 27. The beam 26 passes through the analyte and thereby a pattern of diffracted radiation 28. A suitable detector 25 for the diffracted radiation is placed vertically below said support 23. The detector 25 is coupled to a recorder (not shown) for recording the pattern of each specific analyte.

In order to analyse each of the analytes 24 in the support 23 a displacement device 39 is provided, in this example a device 29 allowing movement of the support 23 in a horizontal plane, so that each of the analytes 24 can be brought into the beam 26 for analysis of said analyte 24. The device 29 preferably allows for an automatic displacement of the support 23 so that all the analytes 24 on the support 23 are analysed successively.

Figure 3:
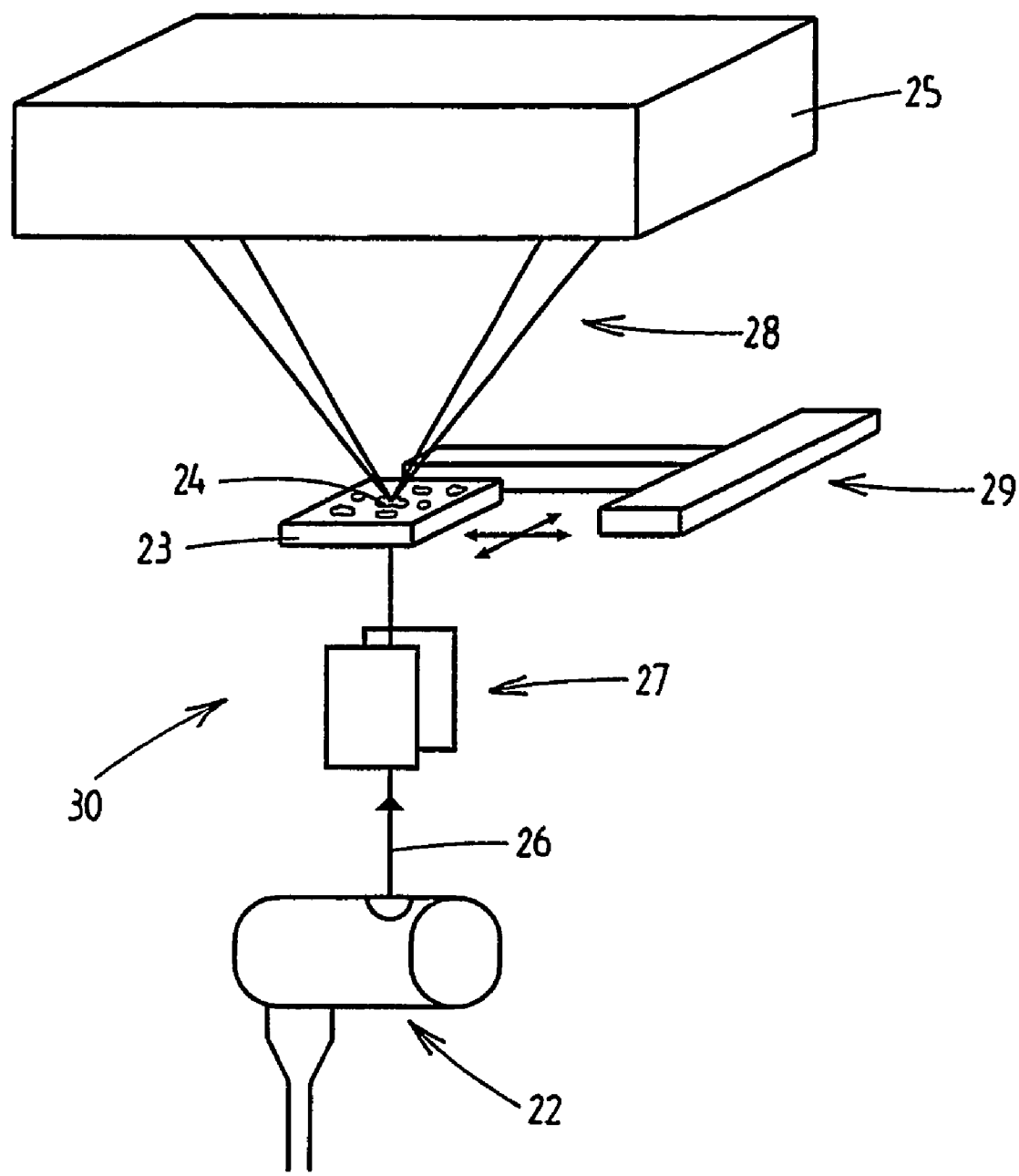
FIG. 3 shows schematically an alternative preferred embodiment of a transmission diffraction analysis apparatus according to the invention.

FIG. 3 shows the transmission diffraction analysis apparatus 30, which apparatus 30 basically includes the same components as the apparatus 20. In the apparatus 30 however the radiation source 22 is placed below the support 23 and generates a vertically upward directed beam 26, which strikes an analyte 24 from below. The detector 25 is now arranged above the support 23 for receiving the upward directed pattern of diffracted radiation.

The support 23 preferably has a container for each analyte, which container is translucent for the radiation, at least the part of the container forming the support surface for the analyte. In a preferred embodiment the container is open at the top during the analysis, however it is also envisaged that the containers are closed.

In a preferred embodiment the analytes are crystallised in their containers prior to the diffraction analysis, so that the analytes do not need to be transferred between the step of crystallisation and transmission diffraction analysis.

In a practical embodiment the support 23 is a plate having a plurality of wells each forming a container for receiving an analyte.

It is also preferred that the support is translucent for visual light.

It is envisaged that the method includes the step of determining the background diffraction pattern of the support and the step of correcting the measured pattern for this background diffraction pattern.

In an embodiment not show in the drawings means are provided for controlling the atmospheric conditions.

Also it is possible to provide heat transfer means for controlling the temperature of the analyte, e.g. for effecting phase change of the analyte or drying of the analyte during the transmission diffraction analysis.

The invention claimed is:

1. A method for performing a transmission of diffraction analysis of one or more analytes on a support having a support surface, wherein the method comprises:

providing one or more analytes on a support having a support surface;

providing a source of radiation vertically above or vertically below said support surface;

providing a detector vertically below or vertically above said support surface such that said support surface is positioned between said source of radiation and said detector;

irradiating each of said analytes with a radiation beam generated by the source of radiation, said radiation beam being directed onto said analyte, thereby creating a pattern of diffracted radiation; and detecting said diffracted radiation with said detector after said diffracted radiation passes through the analyte, and determining the diffraction pattern of the analyte, wherein said irradiation is performed such that the radiation beam strikes the analyte in a substantially vertical and substantially perpendicular direction in relation to the support surface.

2. The method according to claim 1, wherein the support surface is essentially horizontal.

3. The method according to claim 1, wherein a plurality of analytes is placed on the support.

4. The method according to claim 1, wherein a plurality of analytes is placed on the support, and wherein during the analysis the support is moved with respect to the beam automatically so that successively each of the analytes is radiated by said beam.

5. The method according to claim 1, wherein a plurality of analytes is placed on the support, and wherein the plurality of analytes is placed in an array.

6. The method according to claim 1, wherein a plurality of analytes is placed on the support, and wherein the plurality of analytes is placed in a 2-dimensional array.

7. The method according to claim 1, wherein the one or more analytes are placed on the support in the absence of any additional attachment.

8. The method according to claim 1, wherein the support comprises for each analyte a container containing the analytes, and wherein each container is translucent for the radiation.

9. The method according to claim 1, wherein the support comprises for each analyte a container containing the analyte, and wherein each container is translucent for the radiation, and wherein multiple containers are provided in said support.

10. The method according to claim 1, wherein the support comprises for each analyte a container containing the analyte, and wherein each container is translucent for the radiation, and wherein multiple containers are provided in said support, and wherein each container is filled with a different analyte.

11. The method according to claim 1, wherein the support comprises for each analyte a container containing the analyte, and wherein each container is translucent for the radiation, and wherein the container is open at the top during the analysis.

12. The method according to claim 1, wherein the support comprises for each analyte a container containing the analyte, and wherein each container is translucent for the radiation, and wherein the containers are arranged in an array.

13. The method according to claim 1, wherein the support comprises for each analyte a container continuing the analyte, and wherein each container is translucent for the radiation, and wherein the analyte is crystallised in said container prior to the diffraction analysis.

14. The method according to claim 1, wherein the support comprises for each analyte a container containing the analyte, and wherein each container is translucent for the radiation, and wherein the support is a plate having a plurality of wells each forming a container for receiving an analyte.

15. The method according to claim 1, wherein the support comprises for each analyte a container containing the analyte, and wherein each container is translucent for the radiation, and wherein the one or more containers are sealed during the analysis.

16. The method according to claim 1, wherein the support is translucent for the radiation.

17. The method according to claim 1, wherein the support is translucent for visual light.

18. The method according to claim 1, wherein the method includes the step of determining the background diffraction pattern of the support and the step of correcting the measured pattern for this background diffraction pattern.

19. The method according to claim 1, wherein the atmospheric conditions are controlled.

20. The method according to claim 1, wherein heat transfer means are used for controlling the temperature of the analyte for effecting phase change of the analyte or drying of the analyte during the transmission diffraction analysis.

21. The method according to claim 1, wherein powder diffraction patterns of the one or more analytes are detected and recorded.

22. The method according to claim 1, wherein phase behaviour of the one or more analytes is screened.

23. The method according to claim 1, wherein polymorphism of the one or more analytes is detected.

24. An apparatus for performing a transmission diffraction analysis of an analyte, wherein the apparatus comprises:
   a source of radiation being adapted to direct a radiation beam to the analyte;
   a support for supporting the analyte, which support is translucent to the radiation; and
   a detector for detection of the radiation passed through the analyte,
   wherein the source of radiation, the support for the analyte and the detector are positioned such that the radiation beam generated by the source of radiation can strike the analyte in a substantially vertical and substantially perpendicular direction and further wherein said source of radiation is vertically above or vertically below said support and said detector is vertically below or vertically above said support, said support being disposed between said source of radiation and said detector.

25. The apparatus according to claim 24, wherein the support is designed for supporting a plurality of analytes.

* * * * *

UNITED STATES PATENT AND TRADEMARK OFFICE
Certificate

Patent No. 7,079,621 B2                          Patented: July 18, 2006

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Erwin Blomsma, Haarlem (NL); Adriaan Jan van Langevelde, Almere (NL); and Jan Pieter Abrahams, Leiden (NL).

Signed and Sealed this Second Day of July 2013.

<div style="text-align: right;">

TOAN TON
*Supervisory Patent Examiner*
Art Unit 2882
Technology Center 2800

</div>